US009285670B2

(12) United States Patent
Wang et al.

(10) Patent No.: US 9,285,670 B2
(45) Date of Patent: Mar. 15, 2016

(54) DATA COMMUNICATION BETWEEN CAPSULATED CAMERA AND ITS EXTERNAL ENVIRONMENTS

(75) Inventors: Kang-Huai Wang, Saratoga, CA (US); Chung-Ta Lee, Sunnyvale, CA (US)

(73) Assignee: Capso Vision, Inc., Saratoga, CA (US)

(*) Notice: Subject to any disclaimer, the term of this patent is extended or adjusted under 35 U.S.C. 154(b) by 1180 days.

(21) Appl. No.: 11/855,937

(22) Filed: Sep. 14, 2007

(65) Prior Publication Data
US 2009/0073273 A1    Mar. 19, 2009

(51) Int. Cl.
H04N 5/228    (2006.01)
G03B 41/00    (2006.01)
A61B 1/00    (2006.01)
A61B 1/04    (2006.01)

(52) U.S. Cl.
CPC ............ *G03B 41/00* (2013.01); *A61B 1/00016* (2013.01); *A61B 1/041* (2013.01); *A61B 1/042* (2013.01)

(58) Field of Classification Search
CPC .... A61B 1/00016; A61B 1/041; A61B 1/042; G03B 41/00
USPC ................ 348/222.1, 77, 65, 14.02, 211.2; 235/462.11, 462.24
See application file for complete search history.

(56) References Cited

U.S. PATENT DOCUMENTS

| 4,278,077 A | 7/1981 | Mizumoto |
| 5,247,166 A * | 9/1993 | Cannon et al. ............. 250/208.1 |
| 5,550,363 A * | 8/1996 | Obata ....................... 235/462.11 |
| 5,604,531 A | 2/1997 | Iddan et al. |
| 6,157,455 A * | 12/2000 | Pinvidic et al. ................ 356/437 |
| 6,428,469 B1 | 8/2002 | Iddan et al. |
| 6,484,933 B1 * | 11/2002 | Zimmerman et al. ........ 235/375 |
| 6,709,387 B1 | 3/2004 | Glukhovsky et al. |
| 6,800,060 B2 | 10/2004 | Marshall |
| 7,009,634 B2 | 3/2006 | Iddan et al. |
| 7,065,288 B1 | 6/2006 | Xue |

(Continued)

FOREIGN PATENT DOCUMENTS

| EP | 1 610 485 | 12/2005 |
| WO | 2007/002697 | 1/2007 |

OTHER PUBLICATIONS

PCT International Search Report for International Application No. PCT/US2008/076127 dated Nov. 17, 2008, 4 pages.

(Continued)

*Primary Examiner* — Amy Hsu
(74) *Attorney, Agent, or Firm* — Edward C. Kwok; Hogan Lovells US LLP

(57) ABSTRACT

A method for transmitting data to a camera without requiring in the camera a conventional wireless transmission capability includes (a) in the camera's field of view, providing an object which forms an image on which the data is encoded; (b) capturing an image of the object using optics of the camera; and (c) recovering the data from the image of the object. The data is encoded by an optically detectable quantity (e.g., light intensity or color) or a pattern in one or more portions of the object. The data can be carried by the distribution of the optically detectable quantity within the image or its derivative. The field of view of the camera may be divided into multiple sub-areas to allow providing multiple data-bearing images. A sequence of such images may be used to increase the amount of data that can be transmitted in this manner.

35 Claims, 12 Drawing Sheets

(56) References Cited

U.S. PATENT DOCUMENTS

| | | | |
|---|---|---|---|
| 7,138,991 B2* | 11/2006 | Tsuji | 345/204 |
| 7,187,049 B2* | 3/2007 | Sarwari | 257/431 |
| 7,489,346 B2* | 2/2009 | Mizukura et al. | 348/223.1 |
| 7,495,993 B2* | 2/2009 | Wang | 365/230.09 |
| 7,630,015 B2* | 12/2009 | Okamura | 348/371 |
| 7,692,630 B2* | 4/2010 | Natsume et al. | 345/158 |
| 7,787,928 B2* | 8/2010 | Frisch et al. | 600/407 |
| 2003/0117491 A1* | 6/2003 | Avni et al. | 348/77 |
| 2004/0211836 A1* | 10/2004 | Patel et al. | 235/462.11 |
| 2005/0012840 A1* | 1/2005 | Hsieh et al. | 348/308 |
| 2005/0173616 A1* | 8/2005 | Jang | 250/208.1 |
| 2006/0150113 A1* | 7/2006 | Natsume et al. | 715/763 |
| 2007/0091713 A1* | 4/2007 | Wang | 365/233 |
| 2007/0098379 A1 | 5/2007 | Wang et al. | |
| 2007/0115378 A1* | 5/2007 | Wang | 348/308 |
| 2007/0116119 A1* | 5/2007 | Wang | 375/240.12 |
| 2009/0073273 A1* | 3/2009 | Wang et al. | 348/222.1 |
| 2013/0044254 A1* | 2/2013 | Tzur | 348/345 |

OTHER PUBLICATIONS

PCT Written Opinion of the International Searching Authority for International Application No. PCT/US2008/076127 dated Nov. 17, 2008, 6 pages.

Supplementary European Search Report for EP08831022.2; dated May 24, 2012, 6 pages.

* cited by examiner

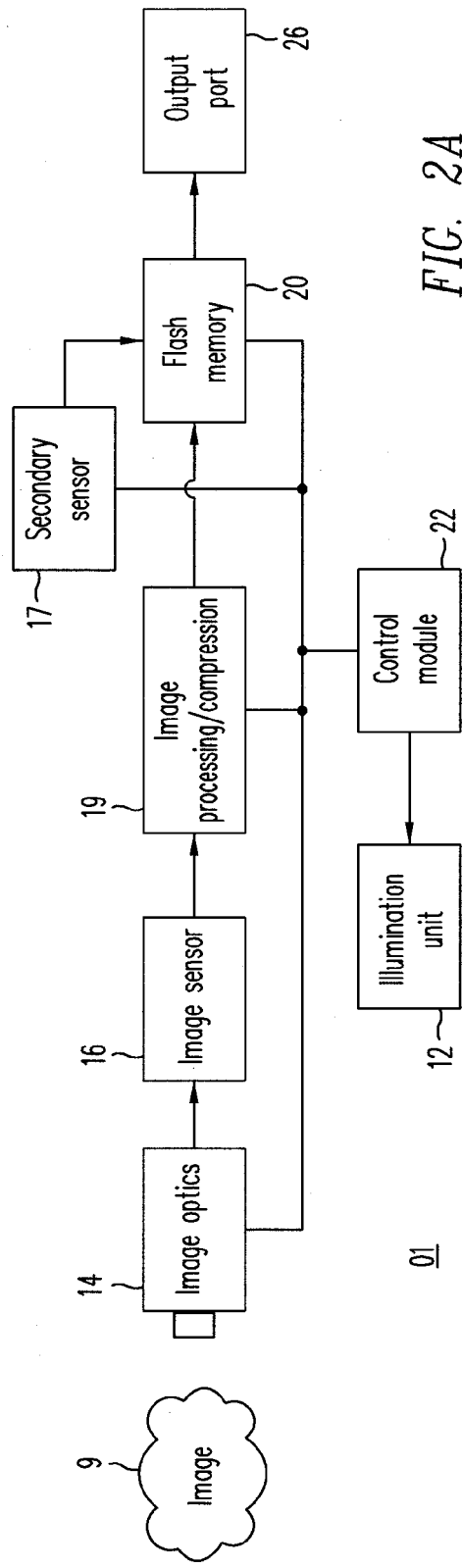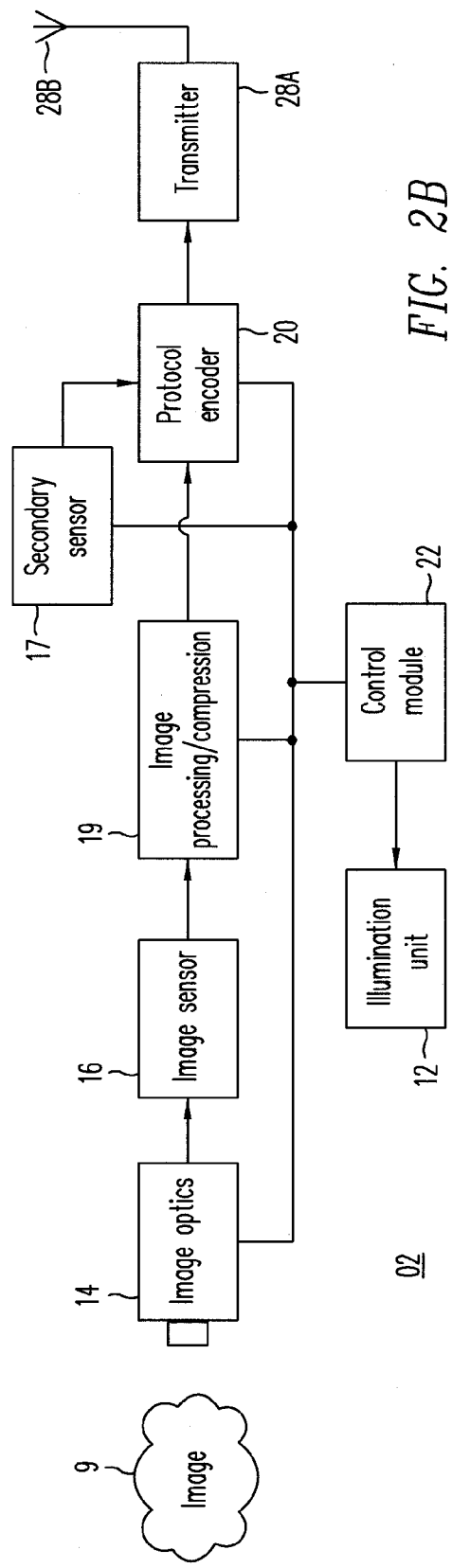

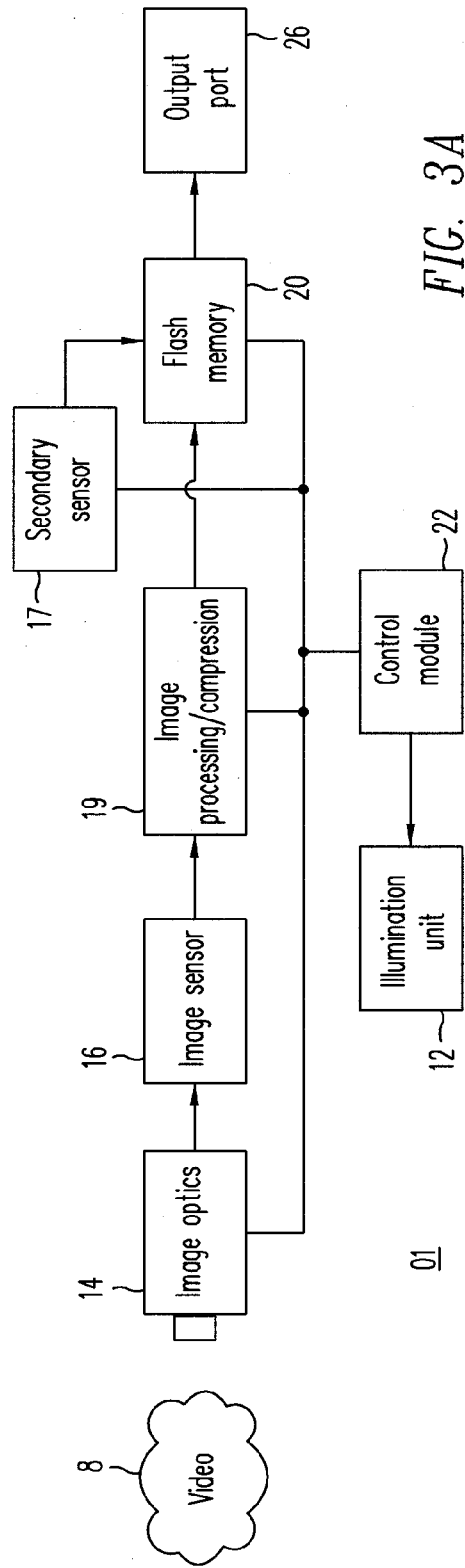
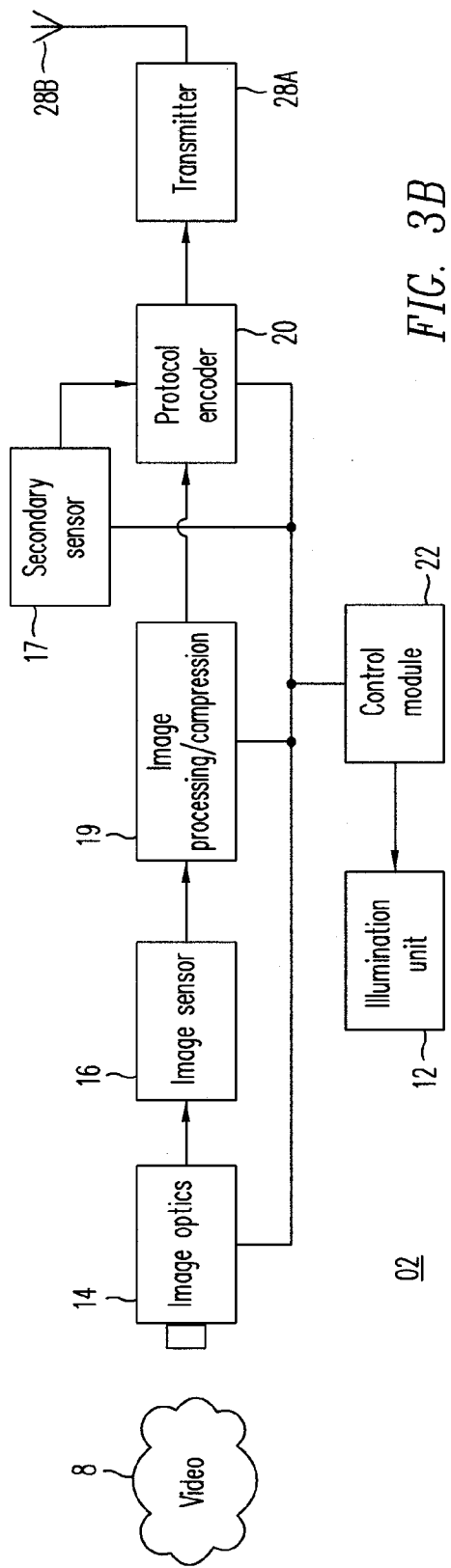
FIG. 3A
FIG. 3B

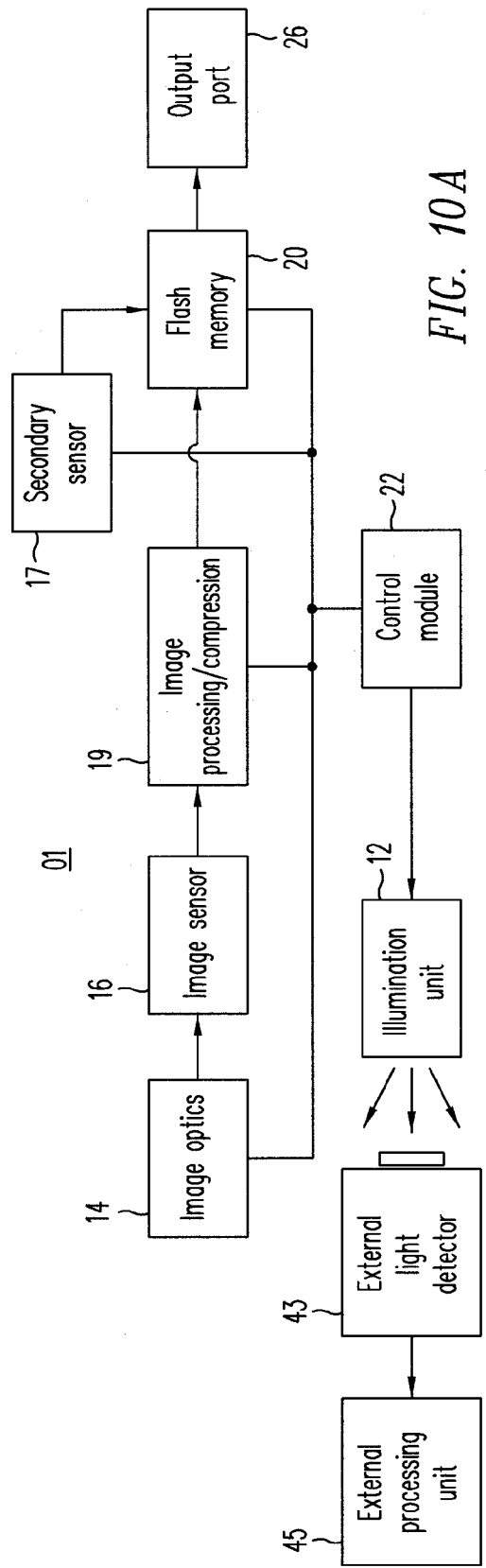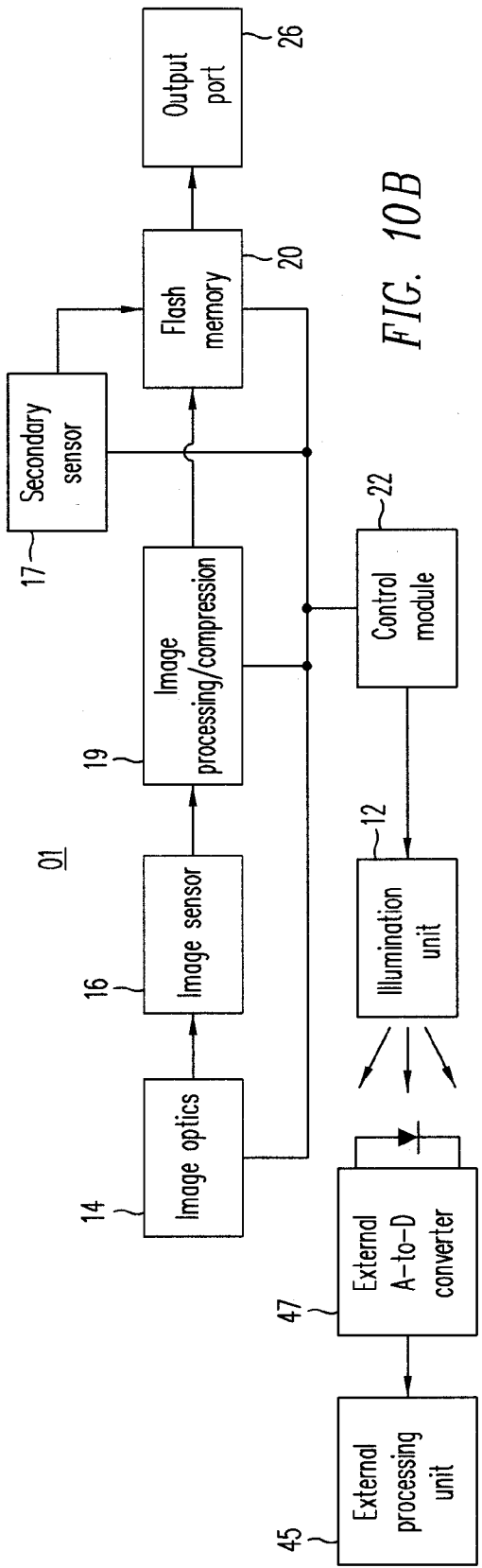
FIG. 10A
FIG. 10B $80 =< V11 =< 88$    $50 =< V12 =< 57$    $23 =< V13 =< 28$    $100 =< V14 =< 110$ $165 =< V21 =< 177$    $120 =< V22 =< 130$    $60 =< V23 =< 66$    $180 =< V24 =< 193$ $40 =< V31 =< 46$    $80 =< V32 =< 88$    $55 =< V33 =< 62$    $170 =< V34 =< 182$ $125 =< V41 =< 135$    $28 =< V42 =< 33$    $100 =< V43 =< 110$    $45 =< V44 =< 51$

DATA COMMUNICATION BETWEEN CAPSULATED CAMERA AND ITS EXTERNAL ENVIRONMENTS

CROSS-REFERENCES TO RELATED APPLICATIONS

Background of the Invention

1. Field of the Invention

The present invention relates to a swallow-able capsule camera for imaging the gastro-intestinal (GI) tract. In particular, the present invention relates to communication by such a capsule camera with its environment, without requiring a conventional radio frequency wireless equipment (e.g., transmitter, receiver or antenna).

2. Discussion of the Related Art

Devices for imaging body cavities or passages in vivo are known in the art and include endoscopes and autonomous encapsulated cameras. Endoscopes are flexible or rigid tubes that are passed into the body through an orifice or surgical opening, typically into the esophagus via the mouth or into the colon via the rectum. An image is taken at the distal end of the endoscope using a lens and transmitted to the proximal end, outside the body, either by a lens-relay system or by a coherent fiber-optic bundle. A conceptually similar instrument may record an image electronically at the distal end, for example using a CCD array or a CMOS array, and transfer the image data as electrical signals to the proximal end through a cable. The endoscope allows a physician control over the field of view and is a well-accepted diagnostic tool. However, endoscopes have a number of limitations, present risks to the patient, and are invasive and uncomfortable for the patient. The cost of these procedures restricts their application as routine health-screening tools.

Because of the difficulty traversing a convoluted passage, endoscopes cannot reach most of the small intestine and special techniques and precautions, thereby adding cost, are required to reach the entirety of the colon. Endoscopic risks include the possible perforation of the bodily organs traversed and complications arising from anesthesia. Moreover, a trade-off must be made between patient pain suffered during the procedure and the health risks and post-procedural down time associated with anesthesia. Endoscopy is necessarily an in-patient service that involves a significant amount of time from the clinicians and thus are costly.

An alternative in vivo image sensor that addresses many of these problems is capsule endoscopy. In capsule endoscopy, a digital camera is housed in a swallowable capsule, along with a radio transmitter for transmitting data—which primarily consists of images recorded by the digital camera—to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An early example of a camera in a swallowable capsule is described in the U.S. Pat. No. 5,604,531, issued to the Ministry of Defense, State of Israel. A number of patents assigned to Given Imaging describe more details of such a system, using a transmitter to send the camera images to an external receiver. Examples are U.S. Pat. Nos. 6,709,387 and 6,428,469. There are also a number of patents to the Olympus Corporation describing a similar technology. For example, U.S. Pat. No. 4,278,077 shows a capsule with a camera for the stomach, which includes film in the camera. U.S. Pat. No. 6,800,060 shows a capsule which stores image data in an atomic resolution storage (ARS) device.

An advantage of an autonomous encapsulated camera with an internal battery is that the measurements may be made with the patient ambulatory, out of the hospital, and with only moderate restrictions of activity. The base station includes an antenna array surrounding the bodily region of interest and this array can be temporarily affixed to the skin or incorporated into a wearable vest. A data recorder is attached to a belt and includes a battery power supply and a data storage medium for saving recorded images and other data for subsequent uploading onto a diagnostic computer system.

A typical procedure consists of an in-patient visit in the morning during which a clinician attaches the base station apparatus to the patient and the patient swallows the capsule. The system records images beginning just prior to swallowing and records images of the GI tract until its battery completely discharges. Peristalsis propels the capsule through the GI tract. The rate of passage depends on the degree of motility. Usually, the small intestine is traversed in 4 to 8 hours. After a prescribed period, the patient returns the data recorder to the clinician who then uploads the data onto a computer for subsequent viewing and analysis. The capsule is passed in time through the rectum and need not be retrieved.

The capsule camera allows the GI tract from the esophagus down to the end of the small intestine to be imaged in its entirety, although it is not optimized to detect anomalies in the stomach. Color photographic images are captured so that anomalies need only have small visually recognizable characteristics, not topography, to be detected. The procedure is pain-free and requires no anesthesia. Risks associated with the capsule passing through the body are minimal—certainly the risk of perforation is much reduced relative to traditional endoscopy. The cost of the procedure is less than the cost for traditional endoscopy, due to the decreased demand on clinician time and clinic facilities, and anesthesia is not required.

As the capsule camera becomes a viable technology for inspecting gastrointestinal tract, various methods for storing the image data have emerged. For example, U.S. Pat. No. 4,278,077 discloses a capsule camera that stores image data in chemical films. U.S. Pat. No. 5,604,531 discloses a capsule camera that transmits image data by wireless to an antenna array attached to the body or provided in the inside a vest worn by a patient. U.S. Pat. No. 6,800,060 discloses a capsule camera that stores image data in an expensive atomic resolution storage (ARS) device. The stored image data could then be downloaded to a workstation, which is normally a personal computer for analysis and processing. The results may then be reviewed by a physician using a friendly user interface. However, these methods all require a physical media conversion during the data transfer process. For example, image data on chemical film are required to be converted to a physical digital medium readable by the personal computer. The wireless transmission by electromagnetic signals requires extensive processing by an antenna and radio frequency electronic circuits to produce an image that can be stored on a computer. Further, both the read and write operations in an ARS device rely on charged particle beams.

A capsule camera using a semiconductor memory device, whether volatile or nonvolatile, has the advantage of being capable of a direct interface with both a CMOS or CCD image sensor, where the image is captured, and a personal computer, where the image may be analyzed. The high density and low manufacturing cost achieved in recent years made semiconductor memory the most promising technology for image storage in a capsule camera. According to Moore's law, which is still believed valid, density of integrated circuits double every 24 months. Meanwhile, CMOS or CCD sensor resolution continues to improve, doubling every few years. Recent advancement in electronics also facilitate development in capsule camera technology. For example, (a) size and power reductions in light emitting diodes (LEDs) promotes the use of LEDs as a lighting source for a capsule camera; (b) new CMOS image sensors also reduce power and component count; (c) the continued miniaturization of integrated circuit allows integrating many functions on a single silicon substrate (i.e., system-on-a-chip or "SOC), resulting in size and power reductions.

One obstacle to overcome in capsule camera production is to perform a complete test after it is assembled and encapsulated in the capsule housing. A test is needed not only after the capsule camera is assembled and housed during the manufacturing process, but also after shipment or after the capsule camera has been in storage for some time. For a capsule camera using on-board memory storage, there is generally no means to communicate by wireless with the outside world. Wireless communication allows test commands to sent and applied under test conditions, or to provide test data from inside the capsule camera to the outside for analysis. For a capsule camera with a wireless capability, typically only a transmitter is provided, but not a receiver, or its corresponding protocol circuitry or software. To include a receiver in a capsule camera would complicate capsule camera design, increase its size and cost.

In addition to the post-encapsulation testing requirements, providing the capsule camera an ability to receive commands, information and data from the outside enables two-ways communication and interaction. This additional capability is desired as it increases the capsule camera's functions, applications and flexibility. For example, with this additional capability, some parameters may be updated, errors may be corrected, and performance can be improved. As another example, such a capability allows a health care practitioner to program the capsule camera to examine specific areas (e.g., the esophagus, the small intestine, the large intestine, or any combination of a number of areas) and customize its operation. For example, the frame rate for imaging the esophagus may be programmed to a different value from a frame rate for the large intestine.

SUMMARY OF THE INVENTION

According to one embodiment of the present invention, a capsule camera having an image sensor and a lighting system (e.g., a CMOS image sensor and an LED lighting system) uses its image sensor and its lighting system to communicate with its external environment, without incurring the cost of equipping it for conventional radio frequency wireless communication (e.g., a transmitter and a receiver). Information, command or data may be received into the capsule camera using its optical system. The image may be presented, for example, by a still object in the field of view of the capsule camera, so as to be captured by the image sensor. Data may be represented by a specific image pattern, consecutive image patterns, or color for the capsule camera to capture, recognize and decode using its image sensor.

The image sensor captures the pattern or sequence of patterns as image data and provides the image data to an application specific integrated circuit (ASIC) which analyzes the captured image data to determine the data, command or information received. In one embodiment, a specific pattern, sequence of patterns, color, or color patterns are provided for capture in an image. The specific pattern, sequence of patterns, color, or color patterns encode commands, data or information. In another embodiment, a specific intensity or intensity pattern, or different images of specific intensities, or intensity patterns presented in a sequence of images may be used to encode command, data or information.

According to another embodiment of the present invention, a video image transmits command, data or information to the capsule camera. The video image may be of a moving or a changing object in the field of view, so as to be captured as video images by the image sensor.

According to another embodiment of the present invention, one or more LEDs may be used to signal to the outside and to transmit data from the capsule camera to an external environment. For example, a specific LED intensity may be used to transmit a specific command, information or data. Alternatively, a sequence of specific intensity flashes by the LED may be used to transmit specific command, information or data. In another embodiment, multiple LEDs with different intensities may be used in concert to transmit a specific set of commands, information or data. As still another example, a sequence of specific intensity flashes by the LED may be used to transmit a specific set of commands, information or data.

In another embodiment of the present invention, a sequence of flashes by multiple LEDs, each providing a different intensity or color, or a combination of intensity and color, may be used to transmit specific commands, information or data.

In another embodiment of the present invention, the duration of the on-time of the LED may be used as another variable. In another embodiment of the present invention, the off-time is used as anther variable.

An LED may be used in a communication protocol when information is communicated between an external source and the capsule camera. For example, an LED signal may serve as an acknowledgement signal or a non-acknowledgement signal in response to data transmitted from the external to the capsule camera. In the opposite direction, the capsule camera's image sensor may detect the optical acknowledgement or non-acknowledgement signal that responds to data transmitted from the capsule camera.

According to one embodiment of the present invention, a method for transmitting data to a camera without requiring in the camera a conventional wireless transmission capability includes (a) in the camera's field of view, providing an object which forms an image on which the data is encoded; (b) capturing an image of the object using optics of the camera; and (c) recovering the data from the image of the object. The data is encoded by an optically detectable quantity (e.g., light intensity or color) or a pattern in one or more portions of the object. The data can be carried by the distribution of the optically detectable quantity within the image or its derivative. The field of view of the camera may be divided into multiple sub-areas to allow providing multiple data-bearing images. A sequence of such images may be used to increase the amount of data that can be transmitted in this manner. In addition, the time domain can be used to create one further dimension of data encoding. In addition, communication in the opposite direction may be provided using one or more lighting devices in the camera. One use is to provide a response (e.g., acknowledgement or non-acknowledgement to the data transmission based on the data recovered). The camera's response may be detected by one or more light detectors outside of the camera. Communication can be carried out using an interactive communication protocol. By providing multiple lighting devices in the camera and multiple light detectors in the outside, the system provides a parallel data bus, which may include a clock signal to govern timing on the bus. The data may be represented as quantized values.

The present invention is better understood upon consideration of the detailed description below in conjunction with the accompanying drawings.

BRIEF DESCRIPTION OF THE DRAWINGS

FIGS. 2A and 2B are functional block diagrams of information flow in a capsule camera during communication from the external to the capsule camera using a still image, in accordance with one embodiment of the present invention.

FIGS. 3A and 3B are functional block diagrams of information flow of a capsule camera during communication from the external to the capsule camera using video, in accordance with one embodiment of the present invention.

FIG. 6A shows a bright single bar in a dark background, while FIG. 6B shows a dark bar in a bright background.

FIG. 10A is a functional block diagram showing information flow during capsule camera 01's operation, when external light detector 43 is presented and placed such that the illumination unit 12 or the light from illumination unit 12 may reach external light detector 43, according to one embodiment of the present invention.

FIG. 10B is a functional flow diagrams of information flow of a capsule camera during communication of data or command from inside the capsule to outside using LED and light detector, in accordance with one embodiment of the present invention.

FIG. 11A show examples of values collected from areas in the first images and values collected from the second images in FIG. 11B; to confirm or jointly provide the information transmitted.

DETAILED DESCRIPTION OF THE INVENTION

For a capsule camera which includes on-board storage, but not a wireless transmitter, or for a capsule camera with a wireless transmitter, but with a secondary data transmission route from the camera to the external, LEDs within the capsule camera may be used to transmit data, command, or information from within the capsule camera to its outside. Also, the image sensor inside the capsule camera, which is capable of capturing images, video, or both, may interpret the captured images or video in a processor to determine if an object seen within its field of view communicates any data, command or information. Since the image sensor and the LEDs are customary components of the capsule camera, using the image sensor and the LEDs to communicate information between the capsule camera and the external adds no additional overhead cost.

Figure 1A:
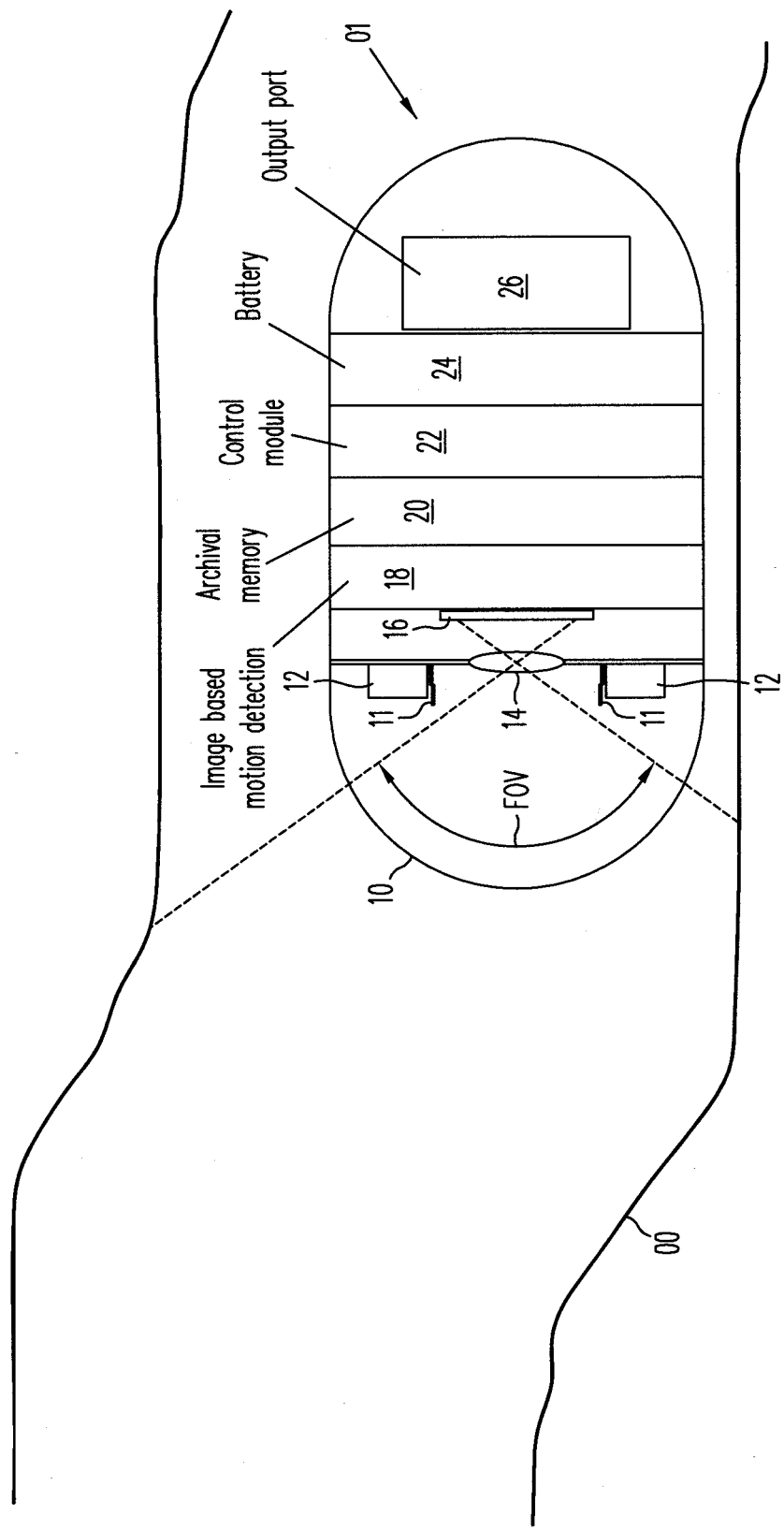
FIG. 1A shows schematically capsule camera 01 with on board memory in the GI tract, showing the capsule in a body cavity.

FIG. 1A shows a swallowable capsule camera 01 inside body lumen 00, in accordance with one embodiment of the present invention. Lumen 00 may be, for example, the colon, small intestines, the esophagus, or the stomach. Capsule camera 01 is entirely autonomous while inside the body, with all of its elements encapsulated in a capsule housing 10 that provides a moisture barrier, protecting the internal components from bodily fluids. Capsule housing 10 is transparent, so as to allow light from the LEDs of illuminating system 12 to pass through the wall of capsule housing 10 to the lumen 00 walls, and to allow the scattered light from the lumen 00 walls to be collected and imaged within the capsule. Baffle or reflector 11 is used to direct the light toward the object and to avoid the light to directly enter into the pupil. Capsule housing 10 also protects lumen 00 from direct contact with the foreign material inside capsule housing 10. Capsule housing 10 is provided a shape that enables it to be swallowed easily and later to pass through of the GI tract. Generally, capsule housing 10 is sterile, made of non-toxic material, and is sufficiently smooth to minimize the chance of lodging within the lumen.

As shown in FIG. 1A, capsule camera 01 includes illuminating system 12 and a camera that includes optical system 14 and image sensor 16. An image captured by image sensor 16 may be processed by image-based motion detector 18, which determines whether the capsule is moving relative to the portion of the GI tract within the optical view of the camera. Image-based motion detector 18 may be implemented in software that runs on a digital signal processor (DSP) or a central processing unit (CPU), in hardware, or a combination of both software and hardware. An optional image-based motion detector 18 may have one or more partial frame buffers, a semiconductor nonvolatile archival memory 20 may be provided to allow the images to be retrieved at a docking station outside the body, after the capsule is recovered. System 01 includes battery power supply 24 and an output port 28. Capsule camera 01 may be propelled through the GI tract by peristalsis.

Illuminating system 12 may be implemented by LEDs. In FIG. 1, the LEDs are located adjacent the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 14, which may include multiple refractive, diffractive, or reflective lens elements, provides an image of the lumen walls on image sensor 16. Image sensor 16 may be provided by charged-coupled devices (CCD) or complementary metal-oxide-semiconductor (CMOS) type devices that convert the received light intensities into corresponding electrical signals. Image sensor 16 may have a monochromatic response or include a color filter array such that a color image may be captured (e.g. using the RGB or CYM representations). The analog signals from image sensor 16 are preferably converted into digital form to allow processing in digital form. Such conversion may be accomplished using an analog-to-digital (A/D) converter, which may be provided inside the sensor (as in the current case), or in another portion inside capsule housing 10. The A/D unit may be provided between image sensor 16 and the rest of the system. LEDs in illuminating system 12 are synchronized with the operations of image sensor 16. One function of control module 22 is to control the LEDs during image capture operation.

Motion detection module 18, if equipped, selects an image to retain when the image shows enough motion relative to the previous image in order to save the limited storage space available. The images are stored in an on-board archival memory system 20. The output port 26 shown in FIG. 1A is not operational in vivo but uploads data to a work station after the capsule is recovered, having passed from the body. Motion detection can also be used to regulate the image capture rate (i.e., the frequency at which the camera captures an image). It is desirable to increase the capture rate when the capsule is in motion. If the capsule remains at the same place, it may be desirable to capture an image less frequently to save battery power.

Figure 1B:
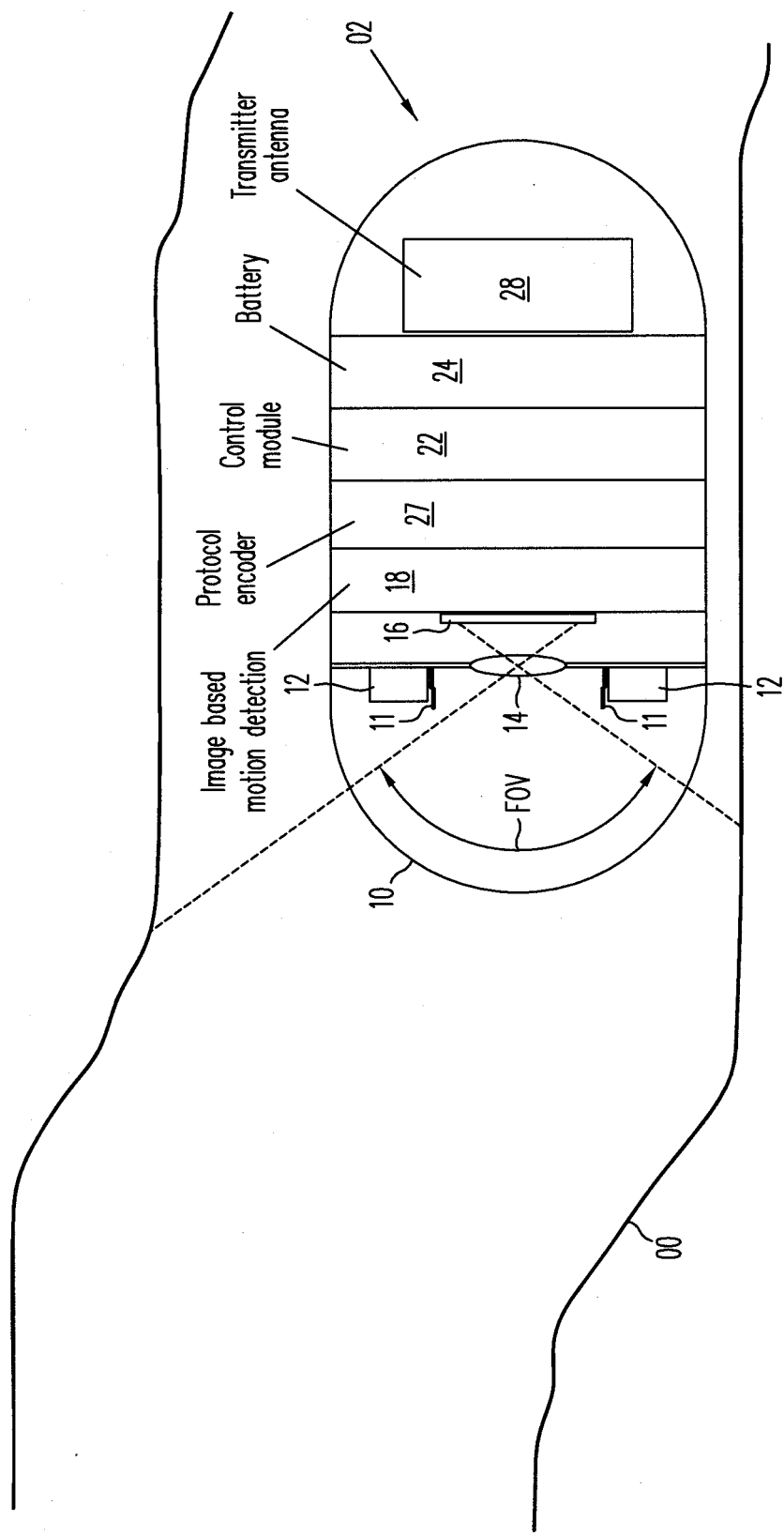
FIG. 1B shows schematically capsule system 02 with a transmitter and an antenna in the GI tract, showing the capsule in a body cavity.

FIG. 1B shows swallowable capsule system 02, in accordance with one embodiment of the present invention. Capsule system 02 may be constructed substantially the same as capsule camera 01 of FIG. 1A, except that archival memory system 20 and output port 26 are no longer required. Capsule system 02 also includes communication protocol encoder 27 and transmitter 28 that are used in the wireless transmission. The elements of capsule 01 and capsule 02 that are substantially the same are therefore provided the same reference numerals. Their constructions and functions are therefore not described here again. Communication protocol encoder 27 may be implemented in software that runs on a DSP or a CPU, in hardware, or a combination of software and hardware, Transmitter 28 includes an antenna system for transmitting the captured digital image.

The above examples in FIGS. 1A and 1B are capsule cameras having lens located at the end looking forward or backward along a longitudinal axis. However, the current invention is applicable to methods that use other ways of implementing optics, such as the panorama optics described in U.S. patent application Ser. No. 11/642,275, and U.S. provisional patent application Ser. No. 60/862,973, filed by Capso Vision, Inc., which disclose systems that capture images of objects located in a direction perpendicular to the longitudinal axis of the capsule camera.

FIG. 2A is a functional block diagram of information flow during capsule camera 01's operation. In addition, an image 9 is shown (symbolically) presented to capsule camera 01 in its field of view. Image 9 may be any 1-dimensional (1-D), 2-dimensional (2-D) or 3-dimensional (3-D) object that forms an image on the image sensor 16 through optical system 14. In capsule camera 01, some images are captured but not stored in archival memory 20, based on decisions made in motion detection circuit 18, which decides whether or not the current image is sufficiently different from the previous image. An image may be discarded if the image is deemed not sufficiently different from the immediately previous stored image. Secondary sensors 17 (e.g., pH, thermal, or pressure sensors) may be provided. The data from image sensor 16, after processing by image processor/compression block 19 or secondary sensors 17, are stored in archival memory system 20. Control module 22, which may consist of a microprocessor, a state machine or random logic circuits, or any combination of these circuits, controls the operations of the modules.

Flash memory system 20 can be implemented by one or more nonvolatile semiconductor memory devices. There are numerous memory types that can be used; even photographic films can be used for image sensing and storage. Since the image data are digitized for digital image processing techniques, such as motion detection, memory technologies that are compatible with digital data are selected. The data in flash memory system 20 may be accessed through output port 26.

In FIG. 2A, during capsule camera 01's normal diagnostic operation inside human body, lighting for capturing the images is provided by illumination system 12. However, when image 9 is provided to communicate data to capsule camera 01 from the outside, lighting is controlled and provided by the external environment, so that an image with a predetermined color and intensity may be captured by image sensor 16, while illumination unit 12 is either turned off or formed only a part of the total lighting.

FIG. 2B is a functional block diagram of information flow during capsule camera 01's operation. In addition, image 9 is shown (symbolically) presented to capsule camera 02 within its field of view. In capsule camera 02, unlike capsule camera 01, an on-board memory is not present, but transmitter 28A and antenna 28B are provided to transmit data to the outside, rather than storing data in a flash memory.

FIG. 3A is a functional block diagram of information flow during capsule camera 01's operation. FIG. 3A also shows (symbolically) video 8 being presented to capsule camera 01 within its field of view. Video 8 may be a sequence of images formed by any 1-D, 2-D or 3-D moving or changing object intended to create a sequence of images in image sensor 16 through optical system 14.

Similarly, FIG. 3B is a functional block diagram of information flow during capsule camera 02's operation. In addition, FIG. 3B also shows (symbolically) video 8 being presented to capsule camera 01 within its field of view. Video 8 may be a sequence of images formed by any 1-D, 2-D or 3-D moving or changing object intended to create a sequence of images in image sensor 16 through optical system 14. In FIG. 3B, an on-board memory is not present, but transmitter 28A and antenna 28B are provided to transmit data to the outside, rather than storing data in a flash memory.

In the systems of FIGS. 2A, 2B, 3A and 3B, lighting in the environment is controlled and provided to present image 9 or video 8 to communicate data to capsule camera 01 or 02. The image, video or object that forms image 9 or video 8 is placed in a predetermined manner and location to achieve the desired image or images in image sensor 16 of capsule camera 01 or 02. In one embodiment of the present invention, a predetermined pattern or sequence of patterns indicate the beginning of a communication session between the external and capsule camera 01 or 02, a header or a delimiter. Another pattern or a sequence of patterns indicates the end of a communication session. A baffle maybe used to avoid cross talk, so that light from the intended source or sources are picked up more precisely.

Figure 4:
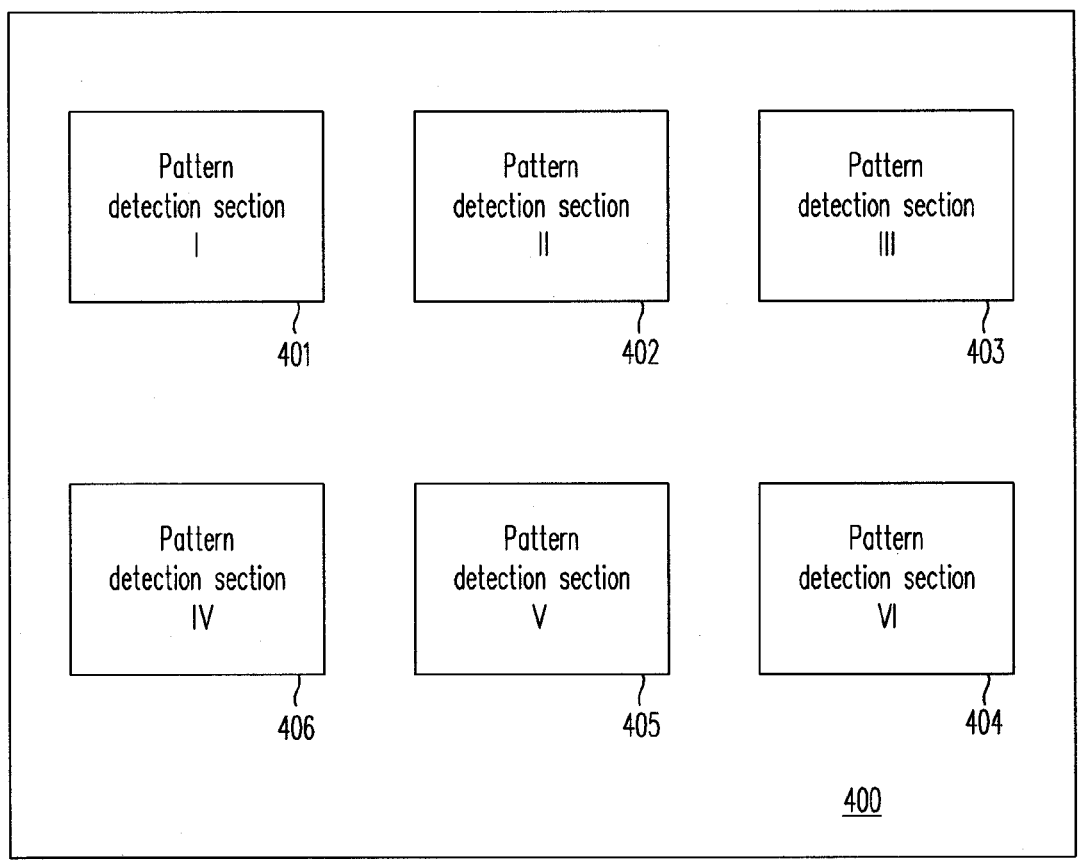
FIG. 4 shows one example of an image for data transmission, in accordance with one embodiment of the present invention.
Figure 5:
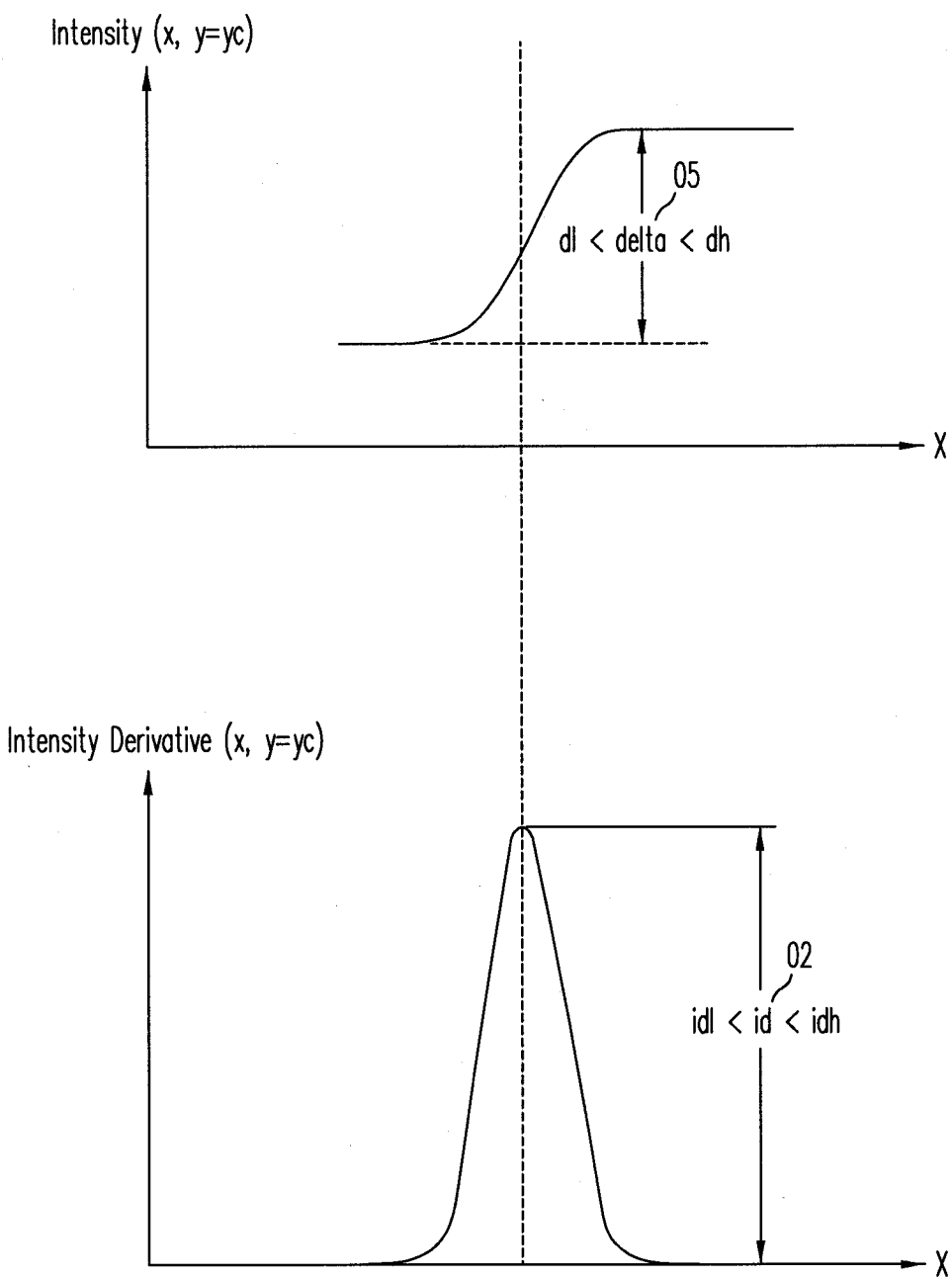
FIG. 5 shows an edge where the intensity increases sharply, and the derivative of the intensity.

The image in FIGS. 2A and 2B may be an image of a still object within the capsule camera's field of view. Similarly, the video in FIGS. 3A and 3B may be a video of a real moving object or a changing object, providing a known sequence of images in the capsule camera's image sensor. In one embodiment of the present invention, the changing object may be an external white LED, color LED, or another light source. Each image or image sequence represents the information transmitted. FIG. 4 shows one example of an image for data transmission, in accordance with one embodiment of the present invention. As shown in FIG. 4, in image 400, the image area is divided into many sub-areas 401-406. The pixel intensity in each area encodes n bits of data (provided the image sensor of the capsule camera has an n-bit intensity resolution). The amount of data transmitted may further be increased many times by the use of colors. The amount of information transmitted depends on the number of sub-areas that can be presented in the field of view of the capsule camera, which depends in turn on sensor pixel size, sensor resolution and the accuracy of the external patterns that may be placed in the sensor field of view. Although shown in FIG. 4 as rectangular, sub-areas 401-406 may be any desired shape. In the case of sub-areas 401-406 of FIG. 4, data used to transmit information may be average, individual pixel intensity or color, and edge differences as shown in FIG. 5. FIG. 5 shows (a) an edge across which (in the x-direction) the light intensity increases sharply, and (b) the derivative of the light intensity along the x-direction. Alternatively local minima or maxima of light intensity may also be used, such as shown in FIG. 6.

One way to create maxima and minima on an image sensor is to have several LEDs and black objects in the camera's field of view. Since the communication between the capsule camera and the external is preferably bi-directional, one method to transmit data, command or information from the capsule camera to the external is to use the camera's LEDs. Under that method, an external light detector or sensor senses the LED light intensity. When the external LEDs are active, the external image sensor or sensors should be disabled from capturing data. Alternatively, the captured data during such time should be accepted as data transmitted from the capsule camera to the external. In one embodiment of the present invention, baffles are used to block crosstalk, so as to enable simultaneous duplex transmission. In another embodiment of the present invention, the impact of the light intensity of the external LEDs or its derivative (e.g. light intensity minima or maxima) on the external image sensor or light detector is subtracted to determine the actual transmitted from the LEDs of the capsule camera.

FIG. 5 shows an example of an edge over which light intensity increases sharply in the x direction. The capsule camera's image sensor detects the data, information or command that is transmitted from the external LED and the corresponding derivative of the intensity. Edge height 05 ("delta 05") represents transmitted data, command or information. In one embodiment, instead of the magnitude of delta 05, the edge height may be quantized to one of several discrete values, depending on which one of several ranges the edge height falls into. Each discrete value represents at least a part of the data, command or information transmitted. As the environment and the equipment used for communication do not have infinite precision, and as variations from one capsule camera to another may exist, a range (instead of a precise numerical value) may be used to represent data, command or information.

In another embodiment of the present invention, one range of the measured value (e.g. an intensity, or a derivative of the intensity, such as a maximum) represents at least a part of a particular data, command or information. The measured ranges are separated in values from each other to avoid error due to the noise in the communication environment, or device to device variations. As shown in FIG. 5, derivative "id 02" may be used as another form to represent at least a part of a data, command, or information. In one embodiment of the present invention, the data, command or information represented is recognized when the following condition is met:

$$d1 = <delta05 = <dh$$

and $$id1 = <id02 = <idh$$

Figure 6A:
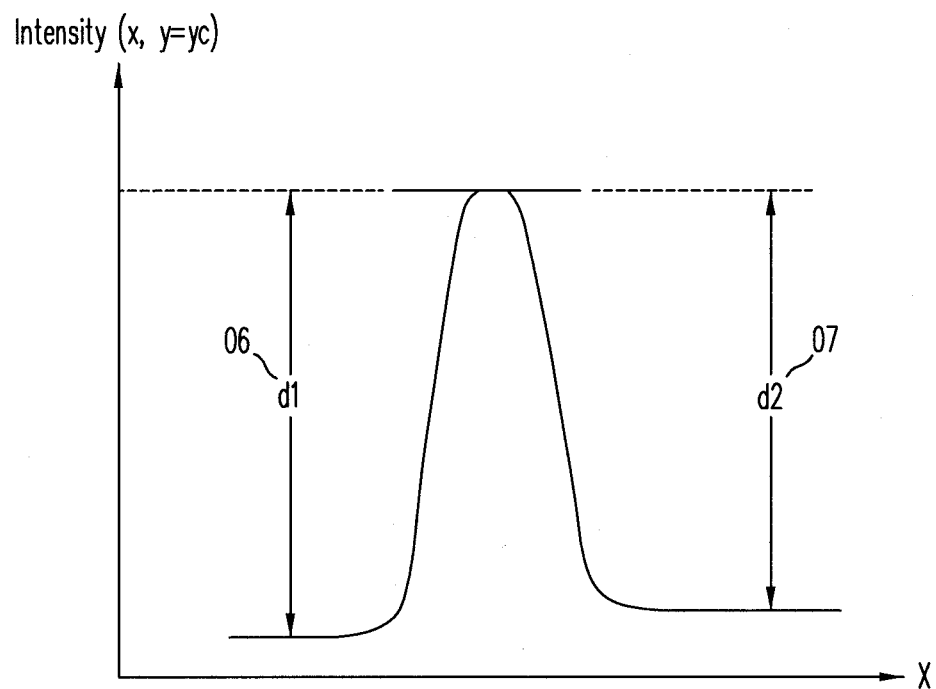
FIGS. 6A and 6B show the intensities of a single bar in a bar code.
Figure 6B:
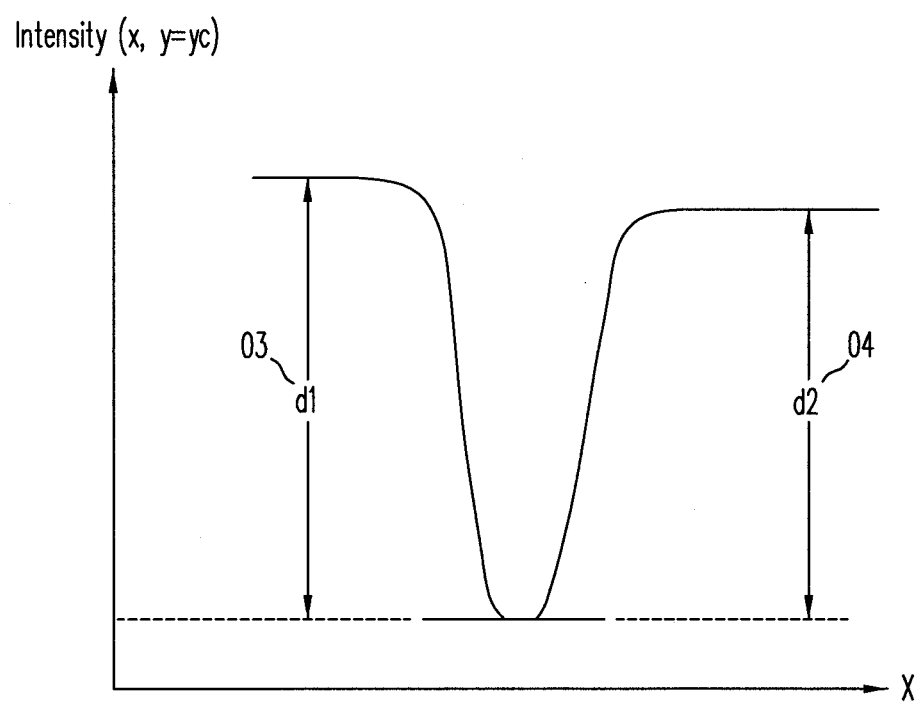

FIGS. 6A and 6B show the intensities of a single bar in a bar code; FIG. 6A shows a bright single bar in a dark background, while FIG. 6B shows a dark bar in a bright background. In addition to their magnitudes, the polarities of d1 06 and d2 07 in FIG. 6A and d1 03 and d2 04 in FIG. 6B (i.e., the directions of increasing or decreasing intensities) may also be used to represent additional information. FIGS. 5 and 6 therefore illustrate two methods that may be used to communicate information to the capsule camera, using the camera's image sensor and taking advantage of pre-defined pattern or object, by placing such pattern or object in the camera's field of view. Other methods include, for example, a simple average light intensity value within a sub-area or a color pattern.

Robust communication practices, such as channel coding, header information, error checking and correction, redundancy bits, start, end, and acknowledgement information may all be transmitted from the capsule camera to the external through its LEDs and from the external to the capsule camera through the capsule camera's image sensor. During transmission from the external to the capsule camera, the camera's LEDs may be used to send acknowledgement or non-acknowledgement information from the capsule camera back to the external. Similarly, the capsule camera's image sensor may be used to receive acknowledgement or non-acknowledgement information from the external to the capsule camera in response to data transmitted from the capsule camera.

Figure 7:
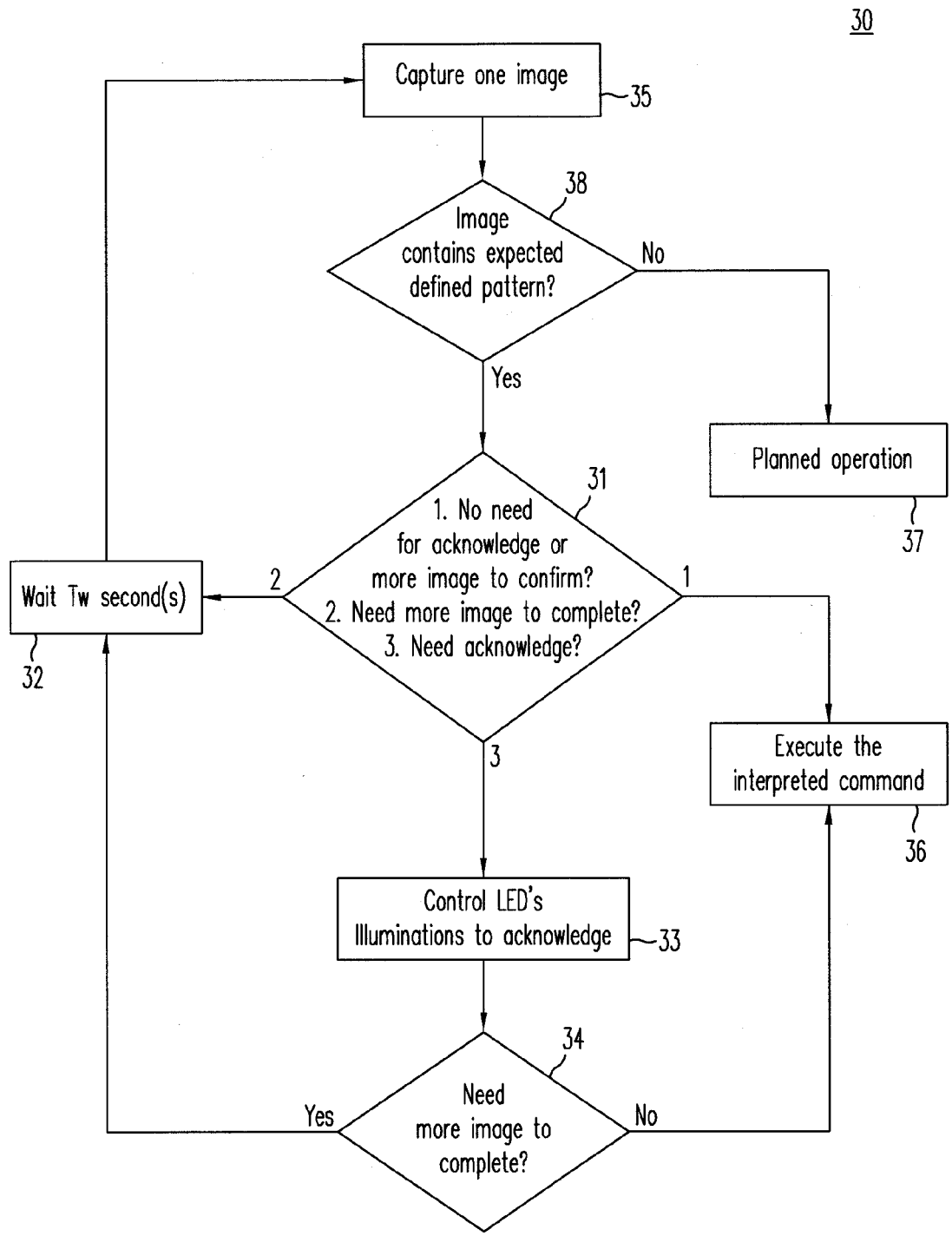
FIG. 7 is a flow chart showing an exemplary communication session in which a command is transmitted from the outside to the capsule camera, in accordance with one embodiment of the present invention.

FIG. 7 is a flow chart showing an exemplary communication session in which a command is transmitted from the outside to the capsule camera, in accordance with one embodiment of the present invention. After an image is captured (step 35), image sensor 16 sends the captured image data to image processor 19 for analysis (step 38), so as to detect any expected, pre-defined pattern. If the image data does not contain the pre-defined patterns, the capsule camera continues its normal operation at step 37.

During the communication session, data and information may be transmitted (e.g., an acknowledgment protocol or header) which are more critical than other data or information. Such data or information, which can tolerate only a low error rate, may be transmitted with (a) highly improbable image pattern combinations (i.e., image pattern combinations designed such that confusion is unlikely with image patterns that the capsule camera encounters under normal operations), (b) high redundancy, error checking and correction in the space domain.

In one embodiment of the present invention, the time domain may be used to lower the error rate using patterns provided at different points in time (see, e.g., step 31). According to another embodiment, the image patterns may be varied at different times according to a predetermined rule. Where multiple images are required to complete transmission of the data, a time interval (e.g., step 32) separates the expected patterns. Such time interval allows the communication setup to replace an image before the next capsule camera exposure and image taken. In one embodiment, if the next expected image or pattern is not shown within the time interval, a time-out event occurs, requiring the communication session to be restarted (not shown in FIG. 7).

For a critical event (e.g., a critical command, a start of transmission or an end of session), the transmission/acknowledgement transaction (steps 31 and 33) may be performed multiple times interactively to ensure robustness in the communication. For example, when a command or a start pattern or a sequence of start patterns from the external is detected by the capsule camera's image sensor, the camera's LEDs provide an acknowledgement (step 33) by one or more flashes in a predetermined manner. After receiving the acknowledgement form the camera's LEDs, another start pattern or sequence of patterns may be sent (step 34). This new pattern or sequence of patterns may be different from the previous pattern or sequence of patterns. The camera's LEDs may acknowledge again (step 33) using, for example, a different LED pattern or sequence of patterns. Thus, a multi-layer protocol may be used to start a session and to provide corresponding acknowledgement. Such a protocol may be used not only for commands or for communicating a start of transmission; it may be used for any command or data. Such a protocol may also be used when data is transmitted from the capsule camera to the outside, such as shown in FIGS. 8-10.

Figure 8:
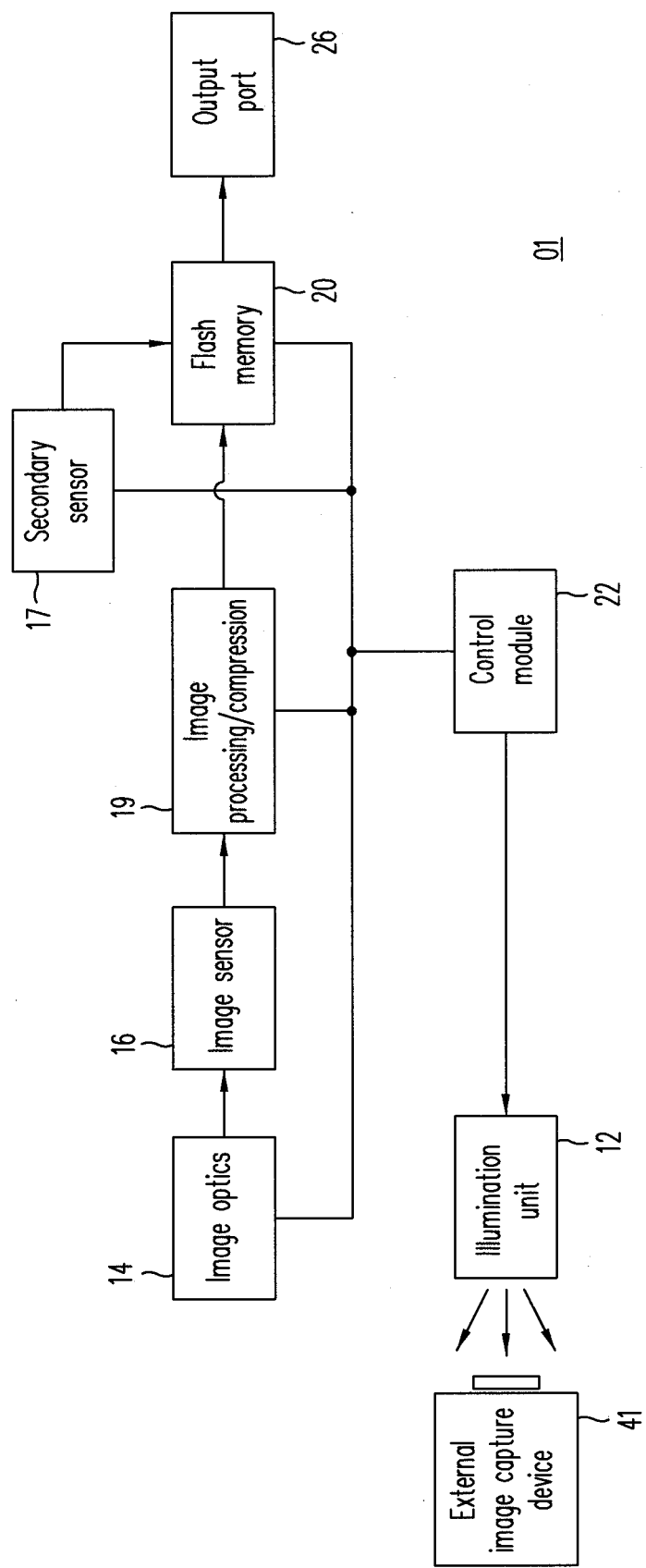
FIG. 8 is a functional block diagram showing an information flow during capsule camera 01's operation, when external image capture device 41 is presented and placed to detect illumination from illumination unit 12 or when light from illumination unit 12 is within external image 41's field of view, in accordance with on embodiment of the present invention.

FIG. 8 is a functional block diagram showing information flow during capsule camera 01's operation, when external image capture device 41 is presented and placed to detect illumination from illumination unit 12 or when light from illumination unit 12 is within external image 41's field of view. Image data received from the capsule camera by external image capture device 41 is forwarded to a processor (not shown) for interpretation. Data sent from the capsule camera may be encoded by light intensity, color, or their changes, along with the time of illumination by the capsule camera's illumination unit 12. Control module 22, which may consist of a microprocessor, a state machine or random logic circuits, or any combination of these circuits, controls the operations of the illumination unit 12. Control module 12 may control the illumination unit 12 based on data store in flash memory 20. In FIG. 8, the lighting condition in the environment during communication between the capsule camera and external image capture device 41 is controlled. For example, the location and orientation of external image capture device 41 relative to capsule camera 01 are provided in a manner such that a known predetermined desired signal level is achieved on the image sensor in external image capture device 41.

Figure 9:
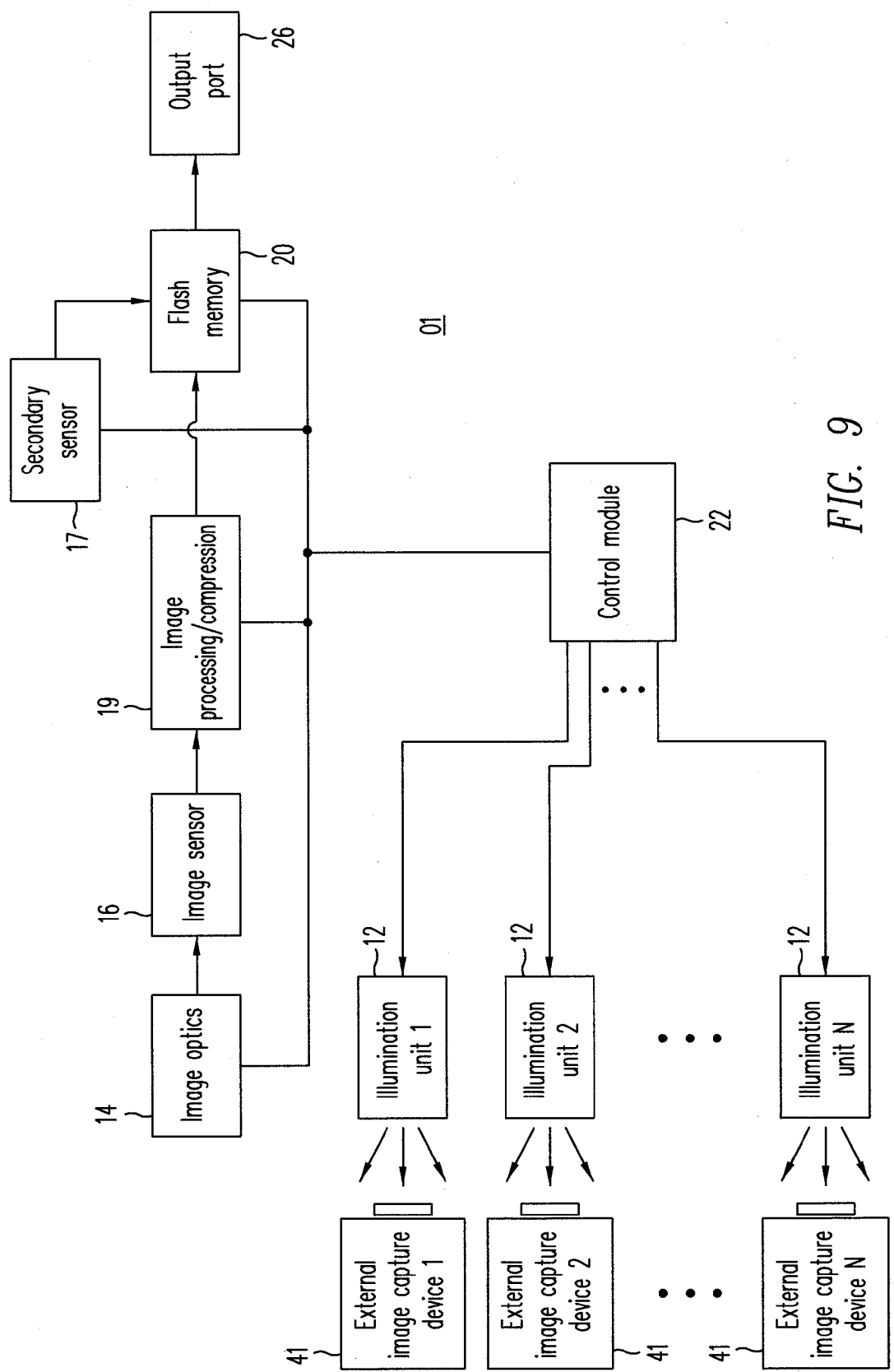
FIG. 9 is a functional block diagram showing information flow in capsule camera 01's operations when multiple external image capture devices 41 and N illumination units 12 are presented and positioned such that each of illumination units 12, or the light from each of illumination units 12, is within the field of view of one or more of external image capture devices 41, according to one embodiment of the present invention.

FIG. 9 is a functional block diagram showing information flow in capsule camera 01's operations when multiple external image capture devices 41 and N illumination units 12 are presented and positioned such that each of illumination units 12, or the light from each of illumination units 12, is within the field of view of one or more of external image capture devices 41. The data from each of external image capture devices 41 are provided to a processor (not shown) for processing. The information sent from capsule camera 01 to external capture devices 41 may be encoded by light intensity, color, or their changes along with the time of illumination. Control module 22, which may consist of a microprocessor, a state machine or random logic circuits, or any combination of these circuits, controls the operations of each of illumination units 12. Control module 22 may control illumination units 12 based on the data store in flash memory 20. The number of external image capture devices 41 need not be the same as the number of internal illumination units 12. Further, one or more processors may be used to analyze and decode the information transmitted by illumination units 12 to external image capture devices 41. In one embodiment, baffles may be used to avoid crosstalk, so that light from illumination units 12 are more precisely detected at external image capture devices 41.

The techniques discussed above relating to the protocol and methods of FIGS. 5-8 are equally applicable to each of illumination units 12 and each of image capture devices 41. In the arrangement of FIG. 9, different LEDs intensities may represent different data values. For example, the N LEDs used for transmitting data in illumination units 12 of FIG. 9 may be organized to form an N-bits wide bus. It is also possible to arrange a combination of LEDs intensities out of these N LEDs to represent one value or a value set. Further, one or more LEDs may vary their intensities to represent a value or a set of values.

In one embodiment of the present invention, one of the LEDs may be used to provide a clock signal. Each LED may have several signal levels, so that more than one bit may be represented. Therefore, when two or more LEDs are used, many combinations of intensity are available to represent many possible data values. In one embodiment, one or more LEDs may be used as to provide clock signals. In another embodiment, the clock signals may be used to synchronize between the capsule camera and the external world occasionally, rather than a dedicated clock signal operating 100% of the time. Providing an occasional clock signal allows the LED's bandwidth not to be entirely consumed by the clock signal function. For example, the system may be accurate enough to transmit and receive data every micro-second for $10^6-1$ times, but at every $10^6$ times the accumulated error of the timing system inside and the time system outside may require synchronization to ensure that the next $10^6-1$ transactions are correctly handled. Therefore, the LED clock signal spends only $1/10^6$ of its bandwidth performing a clock function. This technique may be used in both directions in communication.

FIG. 10A is a functional block diagram showing information flow during capsule camera 01's operation. In addition, external light detector 43 is positioned for detecting the light from illumination unit 12. The data received by external light detector 43 is provided to processor 45 to decode the information sent from capsule camera 01. The data may be encoded by intensity, color, or their changes, along with the time of illumination by illumination unit 12. Control module 22, which may consist of a microprocessor, a state machine or random logic circuits, or any combination of these circuits, controls the operations of the illumination unit 12. Control module 12 may control the illumination unit 12 based on data store in flash memory 20.

In FIG. 10B is a functional block diagram showing information flow during capsule camera 01's operation. In addition, photodiode 48 is to detect illumination unit 12, or the light from illumination unit 12, may reach photodiode 48. Unlike FIG. 10A, photodiode 48—rather than light detector 43—serves as a light detector. The signal from photodiode 48 (e.g., a current) is send to A-to-D converter 47, which in turn passes the data to external processing unit 45, where the command, information or data sent by illumination unit 12 is decoded. In one embodiment of the present invention, processing unit 45 has a digital integrator to measure the total light amount received. In another embodiment, an analog integrator may be used to measure the total amount of light received.

The external image or video capture device 41 (FIG. 8) and light detectors 43 and 47 (FIGS. 10A and 10*b*) may co-exist with external image, video, light sources 8 and 9 (FIGS. 2A, 2B, 3A and 3B) to allow duplex or half-duplex data communication between the capsule camera and its environment. In one embodiment of the present invention, neither image 8 nor video 9 occupies the entire field of view of the capsule camera, so that external image or video capture devices 41, light detectors 43 or 47 may be located in the same field of view. In one embodiment, an external LED, or another light source, is used outside of capsule camera's field of view in such a way that its light can be detected by image sensor 16 in capsule camera 01, when external image or video capture devices 41, or light detectors 43 or 47 are within the same field of view. In one embodiment, light from the capsule camera's LEDs in illumination unit 12 is detected by external image or video capture device 41, or light detector 43 or 47, which are placed outside of the field of view of capsule camera 01, since the LEDs' light are designed to cover some areas outside capsule camera 01. To reduce crosstalk between light sources, baffles may be used in either direction of data transmission.

As discussed above, during the communication session between the capsule camera and the outside setup, some data or information transmitted (e.g., acknowledgement and header) are deemed more critical than other data or information. Such data or information demands a low error rate, and thus may be transmitted using very highly improbable image patterns, with high overhead of redundancy and error checking, and correction in the space domain. In one embodiment, the time domain redundancy may be used to reduce the error rate. In another embodiment, the pattern may be altered at different times, with the two images at the different times governed by a predetermined relationship to provide redundancy.

FIGS. 11A and 11B illustrate an example in which two image matrices are derived from two images at two different times. Each entry of an image matrix is an average of the pixel values within a corresponding one of 16 sub-areas. (By comparison, FIG. 4 shows an image having 3×2 sub-areas). As shown in FIGS. 11A and 11B, the values of sub-areas on the left half of these matrices are 10 higher in FIG. 11B than the corresponding values in FIG. 11A. Similarly, on the right half of these matrices, the values are 20 lower in FIG. 11B than the corresponding entries in FIG. 11A. In one embodiment, the locations of the data may be swapped. In another embodiment, the image data on a page are quantized values each corresponding to one of several ranges of light intensity. In one embodiment, the time between images (or image sequence) may be a specific range of times within which the second image may be detected following detection of the first image, with or without a time-out function. These considerations may be applied for both directions of communication.

As discussed above, quantizing a value within a range of values to a single discrete data value is preferred over providing that value as a precise single value, because lighting accuracy, precise object shape and color, and the capsule camera's location in a test environment cannot be controlled to a high precision. The sensor varies from pixel to pixel within a die, from die to die, from wafer to wafer and from lot to lot; any of these variations may contribute to a deviations in the values captured. In one embodiment, the ranges are larger for higher values.

Data or information transmitted may be represented by pixel values or data derived from pixel values (e.g., averages or differences of pixel values). For example, an increasing value or a decreasing value may be represented by a jump or abrupt drop in light intensity along a given direction, which can be read using an edge detection method, such as illustrated by delta 05 shown in FIGS. 5 and 03, 04, 06, 07 in FIG. 6. Alternatively, data may be represented by a difference between optically measurable quantities at two different locations or at different times, or by a mathematical or logical relationship between optically measurable quantities at two or more locations.

In one embodiment, the data transmitted are coded in accordance with a predetermined table or relationship between the code and the data intended to be communicated. The table or relationship may be time-variant, or changing from one pattern or image to the next in a series of patterns or images. In one embodiment, the images or patterns transmitted at a later time are used to confirm images and patterns transmitted at a later time. In one embodiment, the data and the code representing the data have different number of bits. In one embodiment, data is represented by a code having a unique set of values. To communicate data efficiently, data or data set occurring more frequently may be represented by a code having a lesser number of bits than the code representing data or data set that occur less frequently. In one embodiment, the table or relation that is used to decode data depends on the location of the pattern, image or time representing the data within a series of patterns or images. In one embodiment, data is represented according to a code derived from values at two locations, times or combination of locations and times. In one embodiment, the table or relationship varies, depending the date, user ID, password or other information.

Tue above detailed description is provided to illustrate specific embodiments of the present invention and is not intended to be limiting. Numerous variations and modifications within the scope of the present invention are possible. The present invention is set forth in the accompanying claims.

We claim:

1. A method for transmitting data or command to a camera, comprising:
   using optics of the camera, capturing an image of a predetermined pattern presented in the camera's field of view, wherein the image encodes a command or data to be communicated to the camera based on an amount of change in pixel value in a spatial direction;
   using one or more lighting devices in the camera to provide a parallel data bus;
   decoding the captured image to recover the command or data; and
   operating the camera in accordance with the recovered data or in accordance with a result of executing the recovered command.

2. A method as in claim 1, wherein the predetermined pattern comprises optically detectable features.

3. A method as in claim 2, wherein the optically detectable features comprise one or more of the following: light intensity and color.

4. A method as in claim 2, wherein recovering the data comprises analyzing a distribution of the optically detectable features within the image.

5. A method as in claim 2, wherein recovering the data comprises analyzing the change in a distribution of the optically detectable features within the image.

6. A method as in claim 5, wherein the predetermined position is within one of a plurality of predetermined areas of the camera's field of view.

7. A method as in claim 1, wherein the predetermined pattern is multidimensional.

8. A method as in claim 1 wherein the predetermined pattern is positioned at a predetermined position of the camera's field of view.

9. A method as in claim 1, further comprising capturing a second image after a predetermined time interval.

10. A method as in claim 9, further comprising moving predetermined pattern over the predetermined time interval.

11. A method as in claim 9, further comprising changing the predetermined pattern over the predetermined time interval.

12. A method as in claim 11, wherein the data is encoded by an optically detectable feature in one or more portions of the object.

13. A method as in claim 12, wherein the optically detectable-feature comprises one or more of the following: light intensity and color.

14. A method as in claim 12, wherein recovering the data comprises analyzing the distribution of the optically detectable feature within the image.

15. A method as in claim 12, wherein recovering the data comprises analyzing the change in the distribution of the optically detectable feature within the image.

16. A method as in claim 1, wherein the data transmitted comprises one or more of: a command, data or information.

17. A method as in claim 1, wherein the predetermined pattern is illuminated by the external source.

18. A method as in claim 1, further comprising using one or more lighting devices in the camera to provide an acknowledgement signal.

19. A method as in claim 18, wherein the lighting devices transmit data from the camera to an external receiver.

20. A method as in claim 19, further comprising detecting light from the lighting device of the camera using one or more light detectors outside of the camera.

21. A method as in claim 20, wherein each light detector comprises a photodiode and analog-to-digital converter.

22. A method as in claim 20, wherein the light detectors are positioned outside the field of view of the camera.

23. A method as in claim 18, wherein communication with the camera is governed by an interactive communication protocol.

24. A method as in claim 1, wherein the data represent quantized values.

25. A method as in claim 1, wherein information transmitted in said multiple sub-areas is encoded by one or more of intensity, color, and edge difference.

26. A method as in claim 1, wherein each of the one or more lighting devices provides a single bit of information.

27. A method as in claim 1, wherein the spatial differences in pixel values involve pixels in one or more sub-areas of the image.

28. A method as in claim 27, wherein the spatial differences in pixel values encode multiple bits of command or data in each sub-area.

29. A method for transmitting data or command to a camera, comprising:
   using optics of the camera, capturing an image of a predetermined pattern presented in the camera's field of view, wherein the image includes multiple sub-areas which encode a command or data to be communicated to the camera;
   using one or more lighting devices in the camera to provide a parallel data bus;
   decoding the captured image to recover the command or data; and
   operating the camera in accordance with the recovered data or in accordance with a result of executing the recovered command.

30. A method as in claim 29, wherein the one or more lighting devices also provide an acknowledgement signal.

31. A method for transmitting data or command to a camera, comprising:
   using optics of the camera, capturing an image of a predetermined pattern presented in the camera's field of view, wherein the image includes multiple sub-areas which encode a command or data to be communicated to the camera;
   using one or more lighting devices in the camera to provide a clock signal;
   decoding the captured image to recover the command or data; and
   operating the camera in accordance with the recovered data or in accordance with a result of executing the recovered command.

32. A method as in claim 31, wherein the one or more lighting devices also provide an acknowledgement signal.

33. A method for transmitting data or command to a camera, comprising:
   using optics of the camera, capturing an image sequence presented in the camera's field of view that includes one or more predetermined patterns each of which encodes a command or data to be communicated to the camera based on an amount of change in pixel value in a spatial direction;
   using one or more lighting devices in the camera to provide a parallel data bus;
   decoding the captured image sequence to recover the command or data; and
   operating the camera in accordance with the recovered data or in accordance with a result of executing the recovered command.

34. The method as in claim 33, wherein each image in the image sequence includes multiple sub-areas which encode a command or data to be communicated to the camera.

35. A method as in claim 33, wherein the predetermined patterns comprise information represented by images of one or more moving objects in the captured image sequence.

* * * * *